# (12) United States Patent
Voskoboynikov et al.

(10) Patent No.: US 8,129,576 B2
(45) Date of Patent: Mar. 6, 2012

(54) PROTECTION OF SOLID ACID CATALYSTS FROM DAMAGE BY VOLATILE SPECIES

(75) Inventors: Timur V. Voskoboynikov, Arlington Heights, IL (US); Paul T. Barger, Arlington Heights, IL (US); John Q. Chen, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 2250 days.

(21) Appl. No.: 11/171,799

(22) Filed: Jun. 30, 2005

(65) Prior Publication Data

US 2007/0004953 A1 Jan. 4, 2007

(51) Int. Cl.
*C07C 4/02* (2006.01)
(52) U.S. Cl. ........ 585/653; 585/648; 585/950; 422/211; 208/48 AA; 208/48 R
(58) Field of Classification Search .................. 585/648, 585/653, 950; 422/211; 208/48 AA, 48 R
See application file for complete search history.

(56) References Cited

U.S. PATENT DOCUMENTS

| | | | |
|---|---|---|---|
| 3,274,978 A | 9/1966 | Palchik et al. ................. | 122/356 |
| 3,407,789 A | 10/1968 | Hallee et al. ................... | 122/356 |
| 3,647,682 A | 3/1972 | Rabo et al. .................... | 208/120 |
| 3,758,403 A | 9/1973 | Rosinki et al. ................. | 208/120 |
| 4,310,440 A | 1/1982 | Wilson et al. .................. | 252/435 |
| 4,433,188 A | 2/1984 | Hoelderich et al. ........... | 585/640 |
| 4,440,871 A | 4/1984 | Lok et al. ....................... | 502/214 |
| 4,499,055 A | 2/1985 | DiNicolantonio et al. ... | 422/197 |
| 4,499,327 A | 2/1985 | Kaiser ............................ | 585/640 |
| 4,762,958 A | 8/1988 | Martens et al. ............... | 585/613 |
| 4,780,196 A | 10/1988 | Alagy et al. ................... | 208/130 |
| 4,814,067 A | 3/1989 | Gartside et al. ............... | 208/127 |
| 4,828,679 A | 5/1989 | Cormier, Jr. et al. ......... | 208/120 |
| 4,861,743 A | 8/1989 | Flank et al. .................... | 502/214 |
| 4,980,053 A | 12/1990 | Li et al. .......................... | 208/120 |
| 5,095,163 A | 3/1992 | Barger .......................... | 585/640 |
| 5,096,684 A | 3/1992 | Guth et al. ..................... | 423/306 |
| 5,126,308 A | 6/1992 | Barger et al. .................. | 502/214 |
| 5,151,158 A | 9/1992 | Bowen et al. .................. | 196/110 |
| 5,191,137 A | 3/1993 | Beck .............................. | 585/475 |
| 5,326,465 A | 7/1994 | Yongqing et al. ............. | 208/120 |
| 5,523,502 A | 6/1996 | Rubin ............................ | 585/324 |
| 5,656,150 A * | 8/1997 | Reed et al. .................... | 208/48 R |
| 5,914,433 A | 6/1999 | Marker .......................... | 585/313 |
| 2002/0101953 A1 | 8/2002 | Hettiarachchi et al. ........ | 376/306 |
| 2002/0179495 A1 | 12/2002 | Heyse et al. ................... | 208/137 |

* cited by examiner

*Primary Examiner* — Prem C Singh
(74) *Attorney, Agent, or Firm* — Mark Goldberg

(57) ABSTRACT

The invention provides a method to avoid catalyst damage and achieve longer catalyst life by selecting appropriate materials for reactor spacers, liners, catalyst binders, and supports, in particular, by not using crystalline silica-containing and high phosphorus-containing materials, if the presence of even small amount of steam is anticipated. In addition, alkali metals and alkaline earth metals are avoided due to potential damage to the catalyst.

5 Claims, No Drawings

PROTECTION OF SOLID ACID CATALYSTS FROM DAMAGE BY VOLATILE SPECIES

BACKGROUND OF THE INVENTION

This invention relates to a process of making light olefins using a catalyst that has a low level of contamination. More specifically, this invention relates to the making of light olefins by employing a catalyst that retains a defined level of activity by reducing exposure of the catalyst to undesirable contaminants including crystalline silica, phosphates, alkaline metals and alkaline earth metals. These contaminants have been introduced into prior art reactors from refractory materials used within the reactors.

Olefins such as ethylene, propylene, the butenes, and the pentenes are useful in preparing a wide variety of end products including polyethylenes, polypropylenes, polyisobutylene and other polymers, alcohols, vinyl chloride monomer, acrylonitrile, methyl tertiary butyl ether and tertiary amyl methyl ether and other petrochemicals, and a variety of rubbers such as butyl rubber. Ethylene and propylene are two light olefins that are of particular value in producing such end products.

The olefins used in preparing olefin derivative products have traditionally been made by cracking hydrocarbon feedstocks or more recently by catalytically converting oxygenate feedstocks. Cracking of hydrocarbon feedstocks can be accomplished catalytically or non-catalytically. Non-catalytic cracking processes are described, for example, in Hallee et al., U.S. Pat. No. 3,407,789; DiNicolantonio et al., U.S. Pat. No. 4,499,055 and Gartside et al., U.S. Pat. No. 4,814,067. Catalytic cracking processes are described, for example, in Cormier, Jr. et al., U.S. Pat. No. 4,828,679; Rabo et al., U.S. Pat. No. 3,647,682; Rosinski et al., U.S. Pat. No. 3,758,403; Gartside et al., U.S. Pat. No. 4,814,067; Li et al., U.S. Pat. No. 4,980,053 and Yongqing et al., U.S. Pat. No. 5,326,465. Catalytic conversion of oxygenate feedstocks to produce olefins are described, for example in, Kaiser, U.S. Pat. No. 4,499,327; Barger, U.S. Pat. No. 5,095,163 and Hoelderich et al., U.S. Pat. No. 4,433,188.

Olefins which are typically used as feedstock in the preparation of the above described end products are supplied at a relatively high purity to the appropriate reaction unit.

There are a variety of catalytic processes that are carried out at relatively high temperatures in the presence of steam. In particular, solid acid catalysts for various catalytic processes, including, but not limited to, olefin cracking and methanol to olefin conversion are subject to high-temperature (typically, above 400° C.) exposure in the presence of steam, under process and/or regeneration conditions. In the case of regeneration conditions, in which the catalyst is subjected to oxidizing conditions, steam is formed upon combustion of coke. Catalyst degradation, which often occurs upon steaming, is a combination of several processes, such as zeolite dealumination (or, in general, a decrease in the number of acid sites), structural collapse, pores blockage, acid sites poisoning, as well as others. The rapid degradation of catalyst increases the amount of replacement catalyst that is required and can significantly increase operating costs.

In addition to the degradation of the catalyst performance through deposition of coke, it was unexpectedly found that under certain conditions the catalyst would tend to deactivate after a short period of use when catalyst was exposed to high temperature steaming in a quartz reactor. Analysis of the catalyst revealed that the catalyst was covered with a smooth layer of silica which isolated the active reaction sites from the process vapors. Further investigation revealed that the refractory materials used in the reactor were the source of this silica. It has been found that certain contaminants cause such catalyst degradation including commercial refractory materials used for reactor linings such as silicon, phosphorus, alkali and alkali earth metals. Under high temperatures these elements can become mobile and migrate from reactor lining to the catalyst which in turn leads to catalyst degradation and deactivation. The presence of steam can greatly promote the migration process. Previous to the present invention, there was an awareness that more extreme reactions, such as coal gasification which is carried out at temperatures of 982° C. (1800° F.) and pressures of 1034 kPa (150 psia) or more, experienced problems with lining materials leaching and damaging a catalyst. However, the reaction conditions for light olefin production are much lower. The present application describes a method for avoiding the undesired effects of acid sites poisoning and/or pores blockage by volatile silica and phosphorus species.

SUMMARY OF THE INVENTION

In order to reduce problems associated with contaminant build up on the catalyst, this invention provides an environment in which the catalyst is not exposed to high levels of contaminants. By using catalyst supports and binders as well as avoiding exposure of the catalyst to harmful contaminants, catalysts are able to maintain their activity for substantial longer periods of time.

The invention provides a method to avoid catalyst damage and achieve longer catalyst life by selecting appropriate materials for reactor spacers, liners, catalyst binders, and supports, in particular, by not using crystalline silica-containing and high phosphorus-containing materials, if the presence of even small amounts of steam is anticipated. In particular, materials that leach silicon, phosphorus, alkaline metals such as sodium, potassium or lithium or alkaline earth metals such as magnesium or calcium are to be avoided. Ceramic materials that are resistant to loss of such materials may be used.

The invention also provides a process for production of olefins in which materials within a reactor leach less than 20,000 ppm silicon, less than 1,000 ppm phosphorus, less than 1,000 ppm sodium, less than 500 ppm magnesium and less than 500 ppm calcium when this material is subjected to reaction conditions consisting of steaming at 650° C., 0 kPa (0 psig), 100 g/hr water addition, 250 cc/min (0.5 SCFH) nitrogen for 100 hours.

DETAILED DESCRIPTION OF THE INVENTION

This invention provides a system by which an olefin feed stream is produced by a catalyst that retains its activity through lack of exposure to damaging contaminants. The olefin feed stream is ultimately converted to an olefin derivative which is a product made from at least one olefin in the olefin feed stream, especially from ethylene or propylene. An extensive list of examples of olefin derivatives include polyethylene, polypropylene, polyisobutylene, linear alpha olefins and other polymers, aldehydes, alcohols, acetic acid, acrylic acid, vinyl acetate, vinyl chloride monomer, ethylene dichloride, acrylonitrile, methyl tertiary butyl ether and tertiary amyl methyl ether, ethylbenzene, ethylene oxide, cumene, acrolein, allyl chloride, propylene oxide, and a variety of rubbers such as butyl rubber and ethylene-propylene rubbers, and oligomers of ethylene, propylene or butylenes.

The present invention applies to the production of olefins that can be obtained from conventional processes such as various cracking processes such as the cracking of paraffins, naphtha or $C_4^+$ olefins as well as processes which catalytically convert oxygenate compounds including oxygenate to olefins and oxygenate to propylene processes.

In the case of cracking processes, it can be a non-catalytic or a catalytic process. One such non-catalytic process is steam cracking. Steam cracking processes are generally carried out in radiant furnace reactors at elevated temperatures for short residence times while maintaining a low reactant partial pressure, relatively high mass velocity, and effecting a low pressure drop through the reaction zone. Any of the furnaces known to those skilled in the art may be employed. Examples of furnaces which can be used in this invention are described in Bowen et al., U.S. Pat. No. 5,151,158; Palchik et al., U.S. Pat. No. 3,274,978; Hallee et al., U.S. Pat. No. 3,407,789; Alagy et al., U.S. Pat. No. 4,780,196; DiNicolantonio et al., U.S. Pat. No. 4,499,055 and Martens et al., U.S. Pat. No. 4,762,958, the descriptions of which are incorporated herein by reference.

The hydrocarbon feed to the steam cracker can be in the liquid or vapor phase or it can comprise a mixed liquid-vapor phase. The most preferred feedstocks for steam cracking are ethane, propane, butane, naphtha, gas oils, gas condensates and mixtures thereof. The hydrocarbon feedstock is preferably in the vapor phase within the steam cracker.

Alternatively, instead of steam cracking, other well known cracking processes can be employed to produce olefins. Examples of these other cracking processes include thermal regenerative cracking, fluidized bed cracking, fluid catalytic cracking, deep catalytic cracking, and visbreaking.

In this invention, one or more of the above described cracking processes can be employed. The processes can be configured as separate cracking processes to crack different feedstocks, or used in an integrated process such as described in Rubin, U.S. Pat. No. 5,523,502, the description of which is incorporated herein by reference in its entirety.

In one use of the present invention, olefins are obtained from the catalytic conversion of an oxygenate feed. In this process, contaminant levels are significantly lower than those found in prior art olefin forming processes. The preferred olefins produced in such a process are ethylene and propylene.

This oxygenate feedstock preferably comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Examples of suitable oxygenate compounds include, but are not limited to, the following: methanol; ethanol; n-propanol; isopropanol; $C_4$ to $C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, and mixtures thereof.

Oxygenates can be converted to olefins over small pore molecular sieves and zeolite and non-zeolite catalysts having high selectivity to ethylene and/or propylene. Small pore molecular sieves are preferred in this invention. As defined herein, small pore molecular sieves have a pore size of less than about 5.0 angstroms. Generally, suitable catalysts have a pore size ranging from about 3.5 to about 5.0 angstroms.

Silicoaluminophosphate molecular sieves are often used for the conversion of oxygenates to olefins. These sieves generally comprise a three-dimensional microporous crystal framework structure of $[SiO_2]$, $[AlO_2]$ and $[PO_2]$ tetrahedral units. Silicoaluminophosphate molecular sieves are generally classified as being microporous materials having 8, 10, or 12 member ring structures.

It is preferred that the silicoaluminophosphate molecular sieve used in this invention have a relatively low $Si/Al_2$ ratio. In general, the lower the $Si/Al_2$ ratio, the lower the $C_1$ to $C_4$ saturates selectivity, particularly propane selectivity.

In general, silicoaluminophosphate molecular sieves comprise a molecular framework of corner-sharing $[SiO_2]$, $[AlO_2]$ and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), and rare earth ions. Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from about 3 to about 10 angstroms, and are capable of making size selective separations of molecular species. More than two dozen structure types have been reported, including zeolite topological analogues. Among the aluminophosphates that can be included are AlPO-5, AlPO-11, AlPO-16, AlPO-17, AlPO-18, AlPO-20, AlPO-31, AlPO-34, AlPO-35, AlPO-36, AlPO-40, AlPO-41, AlPO-42, AlPO-44, and ALPO-47. A more detailed description of the background and synthesis of aluminophosphates can be found in Wilson et al., U.S. Pat. No. 4,310,440, which is incorporated herein by reference in its entirety. Preferred ALPO structures are ALPO-5, ALPO-11, ALPO-18, ALPO-31, ALPO-34, ALPO-36, and ALPO-46.

The silicoaluminophosphate molecular sieves are synthesized by hydrothermal crystallization methods generally known in the art. See, for example, U.S. Pat. No. 4,440,871; U.S. Pat. No. 4,861,743; U.S. Pat. No. 5,096,684 and U.S. Pat. No. 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100° to 250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by the same means, and dried.

The reaction mixture can contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, or silica or silica sol, and mixtures thereof while avoiding the use of those materials that leach and contaminate the catalyst. These components are also effective in reducing, inter alia, overall catalyst cost, and acting as a thermal sink to assist in heat shielding the catalyst during regeneration, densifying the catalyst and increasing catalyst strength.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the ATLAS OF ZEOLITE STRUCTURAL TYPES, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

Other catalysts are used in other processes to produce olefins. One class of catalysts that are useful in production of olefins is zeolites. Zeolites are complex crystalline aluminosilicates which form a network of $Al_2$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalysts for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof but also materials which contain suitable replacement atoms for such silicon and aluminum atoms.

The catalyst composition preferably comprises about 1% to about 99%, more preferably about 5% to about 90%, and most preferably about 10% to about 80%, by weight of molecular sieve.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

In one embodiment of this invention, a feed containing an oxygenate, and optionally a diluent or a hydrocarbon added separately or mixed with the oxygenate, is contacted with a catalyst containing a SAPO molecular sieve in a reaction zone or volume. The volume in which such contact takes place is herein termed the "reactor," which may be a part of a "reactor apparatus" or "reaction system." Another part of the reaction system may be a "regenerator," which comprises a volume wherein carbonaceous deposits (or coke) on the catalyst resulting from the olefin conversion reaction are removed by contacting the catalyst with regeneration medium.

The method of making the olefin products in this invention can include the making of these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

In addition to the practice of the present invention in connection with processes to convert oxygenates to light olefins, the invention is useful in olefin cracking processes which involve the catalytic conversion of an olefinic feed stream containing intermediate-weight $C_4$ to $C_7$ olefins to a cracked product stream containing light olefins, $C_2$ to $C_3$ olefins. The olefinic feed stream may be obtained from a mid-cut, $C_4$ to $C_8$ range, of a fluid catalytic cracking (FCC) product stream or from a $C_4$ to $C_6$ stream of a steam cracker furnace which contain abundant olefinic species in the desired intermediate weight range. Moreover, a $C_4^+$ product from an MTO unit, which converts oxygenates over a silicoaluminophosphate molecular sieve catalyst to light olefins as described in Marker, U.S. Pat. No. 5,914,433, would also serve well for upgrading overall process selectivity to light olefins. Increased yield of the light-weight olefinic products for all of the processes is provided by sending $C_4$ to $C_8$ medium-weight olefins to an olefin cracking reactor. Depending upon operating conditions, the medium-weight olefins may be $C_4$ to $C_5$-$C_7$ olefins.

Catalysts suitable for olefin cracking comprise a crystalline silicate of the MFI family which may be a zeolite, a silicalite or any other silicate in that family or the MEL family which may be a zeolite or any other silicate in that family. Examples of MFI silicates are ZSM-5 and Silicalite. An example of an MEL zeolite is ZSM-11 which is known in the art. Other examples are Boralite D and silicalite-2 as described by the International Zeolite Association (ATLAS OF ZEOLITE STRUCTURE TYPES, 1987, Butterworths). The preferred crystalline silicates for this application have pores or channels defined by ten oxygen rings and a high silicon/aluminum atomic ratio.

Suitable olefin cracking process conditions include an inlet temperature of around 400° to 600° C., preferably from 520° to 600° C., yet more preferably 540° to 580° C., and an olefin partial pressure of from 10 to 202 kPa absolute (1.5 to 29 psia), preferably from 50 to 152 kPa absolute (7 to 22 psia). Feed olefins undergo quick isomerization, with product distribution close to that of thermodynamic equilibrium. Olefinic catalytic cracking may be understood to comprise a process yielding shorter molecules via bond breakage.

A crystalline silicate catalyst possessing a high silicon/aluminum ratio can achieve a stable olefin conversion with a high propylene yield on an olefin basis of from 20 to 50 wt-%. The MFI catalyst having a high silicon/aluminum atomic ratio for use in the catalytic olefin cracking process of the present invention may be manufactured by removing aluminum from a commercially available crystalline silicate. A typical commercially available Silicalite has a silicon/aluminum atomic ratio of around 120. The commercially available MFI crystalline silicate may be modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the olefin cracking process. Accordingly, following the steaming step, the crystalline silicate used in this process is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of dealumination of the MFI crystalline silicate. In this way by removing aluminum from the MFI crystalline silicate framework and then removing alumina formed therefrom from the pores, the process aims at achieving a substantially homogeneous de-alumination throughout the whole pore surfaces of the catalyst. This reduces the acidity of the catalyst and thereby reduces the occurrence of hydrogen transfer reactions in the cracking process. The reduction of acidity ideally occurs substantially homogeneously throughout the pores defined in the crystalline silicate framework. This is because in the olefin-cracking process hydrocarbon species can enter deeply into the pores. Accordingly, the reduction of acid site density and thus the reduction in hydrogen transfer reactions which would reduce the stability of the MFI catalyst are pursued throughout the whole pore structure in the framework. The framework silicon/aluminum ratio may be adjusted as desired over a wide range, depending upon several parameters, including feedstock cost and capital/utilities cost.

It has been observed that in catalysts that have acid sites that there can be a gradual deactivation of the catalyst over time. In particular, such deactivation has been observed in olefin cracking, methanol to olefin processes and in naphtha cracking processes. The screening test that was used to measure the effect of the refractory lining to lose silica or other contaminants was as follows: A seven-eighths inch diameter tube was used and first a layer of 35 grams crushed refractory material (6 to 10 mesh) and then a layer of 5 grams of spherical gamma alumina ($Al_2O_3$) were placed in the tube in a manner to prevent direct contact or mixing of the material. The experimental results would be a conservative evaluation because due to the crushing of the refractory, the conditions are more extreme than in a reactor where the refractory lining is intact. In a functioning reactor, silica will only be lost from the portions of the refractory material that are both exposed to steam and heated to a sufficient temperature.

The test procedure consisted of passing an air/steam mixture through the tube, first over the refractory material and then over the alumina. The silica deposition on the alumina was then measured. Unless otherwise stated, the steam rate was 400 grams/hour. Most of the tests were conducted at 460° C. (860° F.), approximately the reactor operating temperature and 1103 kPa (160 psig), well above the operating pressure of about 138 kPa (20 psig). The duration of most tests was 50 hours. However, in order to better gauge the effects of exposure time, some samples of refractory material were subjected to test times from 24 to 100 hours. To further evaluate the effects of test temperature and pressure, along with time, some samples were tested at 414 kPa (60 psig) for either 50 or 100 hours at either 460° or 650° C. Prior to each test the silicon content of the refractory and alumina were measured. Silicon was measured so that the test results would be independent of the actual form of the molecule. After the test, the silicon content of the alumina was again measured with the difference being the amount gained during the test.

A listing of the materials tested, test conditions and results are shown in Table 1. From the data, it is shown that the rate of and potential for silica loss is partially dependent on the amount of silica present. Low silica materials do not lose much silica, but a fairly high amount of silica does not necessarily mean a high rate of silica loss. Since silica can be present in several different forms, some of which are more likely than others to leach under the test conditions, the initial silica content does not correlate to the amount of silica deposition on the catalyst. "Free" silica can be lost, while "tied" silica is not lost. Some of the silica will be in the interior of the aggregate grains and will be unlikely to be exposed to steam and leach out. The hydration and/or firing of the refractory can also reduce the amount of free silica because fines are tied up in the resulting cement gel and thus affect the potential for loss. Therefore, the initial silica content alone, while an indicator, is not enough to determine the likelihood that silica will leach from the refractory.

TABLE 1

Si Migration from Commercial Refractories Conditions: 460° C., 1100 kPa (160 psig), 400 g/hr Steam, 50 hr

| Refractory | Si Content | Type (A, M, I) | ppm Si on R-9 Trap Fresh | Steamed |
|---|---|---|---|---|
| a-Alumina | 560 ppm | | 195 | 502 |
| Norton Si—Al | 6% | | 229 | 2380 |
| Resco 17EC | 17% | M | 222 | 1450 |
| Resco 17EC 24 hr | 17% | M | 150 | 448 |
| Resco 17EC 75 hr | 17% | M | | |
| Resco 17EC 100 hr | 17% | M | 150 | 1700 |
| Resco 17EC 400 kPa (60 psig) | 17% | M | 195 | 1128 |
| Resco 17EC-NS | | M | | |
| Resco AA22S | 4.8% | A | 234 | 3572 |
| Resco AA22S-LS | 1.6% | A | 234 | 1557 |
| Resco AA22S-NS | | A | | |
| Resco RS9 | 21% | I | 195 | 1231 |
| Resco RS9 24 hr | 21% | I | | |
| Resco RS9 100 hr | 21% | I | | |
| Resco ABC | 850 ppm | I | 195 | 216 |
| Criterion 96 | 350 ppm | A | 234 | 388 |
| Criterion 98 | 150 ppm | ? | 195 | 220 |
| Kaolite 3300 | 1460 ppm | I | 253 | 339 |
| Fracocrete 3400 | 676 ppm | A | 150 | 207 |
| Kaotab 95C | | A? | | |
| Castable 33 | 0.31% | I | 150 | 168 |
| Castolast Gun Mix | 948 ppm | A | 150 | 167 |
| Castolast G-Adtech | 990 ppm | A | 150 | 158 |
| Castable 141A | | A | | |
| PLAS2-6 | | M | | |
| ALPHA-8 | | M | | |
| APGreen #1 | 0.14% | M | 204 | 302 |
| APGreen #2 | | M | 204 | 199 |

A = Abrasion Resistant, M = Mid-Range, I = Insulating

An olefin cracking catalyst, which is 80% silicalite (pentasil-type zeolite, Si/Al ratio of about 200), 20% silica binder, was subjected to steaming in 1% steam/$N_2$, at 585° C. in a reactor, for different periods of time. Other conditions were tested as well, including 1.7% steam, $H_2$ carrier gas, and 650° C. temperature). Catalysts were tested under the following conditions: 40% isobutylene/60% isobutane feed, 585° C. inlet temperature, 48.3 kPa pressure, and a 16 $hr^{-1}$ LHSV feed rate. When the catalyst deactivated, the deactivation rate did not slow down (i.e. the delta between 0 and 14, 14 and 28, and 28 and 42 days did not decrease), as would be expected if the problem with the catalyst is in some disintegration of the catalyst such as if zeolite dealumination was taking place. While it was possible that other deactivation mechanism(s) contributed to the worsening performance of the catalyst when the steaming was done in a metal reactor, in the absence of quartz, results were quite different. Only slight deactivation was observed for 14 and 27 days of steaming, at similar conditions. Even though the percent of steam for the second experiment was somewhat lower −0.7% vs. 1.0%, it is believed that this difference is not significant and was not the main contributing factor of improved stability.

The presence of quartz in the reactor and of other quartz-containing materials such as chips, or glass wool has been found to be the most significant factor in the deactivation of the catalyst. However, it was found that unlike crystalline quartz, amorphous silica did not cause catalyst damage. This conclusion was supported by the observation that a catalyst that did not suffer from deactivation was used in an olefin cracking reaction and contained amorphous silica as the binder. The negative effect of quartz volatilization manifested itself to a greater extent for catalysts with a low number of acid sites, as the olefin cracking catalyst but for catalysts with higher number of sites, this effect can be less significant or even absent. Characterization of catalysts, deactivated in a first steaming experiment, by Ammonia TPD (temperature programmed desorption) (Table 2), revealed a continuous decrease in the number of Broensted acid sites. Thus, a good correlation between catalytic test and Ammonia TPD, has been demonstrated.

A second example describes substantial damage of MTO catalyst during regeneration in quartz reactor at 520° to 720° C. Characterization data are summarized in Table 2. The 720° C. regenerated sample lost almost all of the mesoporosity in the 20 to 100 angstrom region. XPS showed that the surface Si/Al ratio had greatly increased and SEM micrographs (not shown) revealed appearance of a coating on the catalyst surface. Examination of several quartz reactors showed clear signs of silica erosion in the pre-heat section, confirming this source of silica contamination.

In the practice of the present invention, preventing premature solid acid catalyst deactivation in the presence of steam can be done by careful selection of materials for spacers, catalyst supporting materials, reactor liners, and other materials within the reactor. Use of quartz and other forms of crystalline silica should be especially limited in those instances when the presence of steam is expected.

A third example describes the detrimental effect of mixing a methanol to olefin SAPO-34 catalyst with a spray dried aluminum phosphate material. This MTO catalyst alone under the test conditions used showed a life of 4.6 hours (time to reach 99% conversion of the feed). When the catalyst was mixed with a spray dried aluminum phosphate material, the catalyst only showed 0.5 hour of life. Phosphorus migration from the aluminum phosphate to the catalyst occurred and resulted in poisoning of acid sites on catalyst. The test conditions included the conditions shown in Table 2:

TABLE 2

| Description | mmoles of $NH_3$/g in specified temperature region | | | Total mmol $NH_3$/g |
|---|---|---|---|---|
| | 200°-300° C. | 300°-400° C. | 400°-500° C. | 200°-500° C. |
| Reference extrudate | 0.003 | 0.007 | 0.004 | 0.014 |
| Sample 1 extrudate, steamed 1% $H_2O/N_2$, 585° C., 14 days | 0.002 | 0.005 | 0.004 | 0.011 |
| Sample 2 extrudate, steamed 1% $H_2O/N_2$, 585° C., 28 days | 0.001 | 0.004 | 0.003 | 0.008 |
| Sample 3 extrudate, steamed 1% $H_2O/N_2$, 585° C., 42 days | 0.001 | 0.003 | 0.003 | 0.007 |

| Sample | $NH_3$ TPD mmol $NH_3$/g cat | Pore Volume, cc/g | | Surface Ratio (XPS) | |
|---|---|---|---|---|---|
| | | Micropore | Mesopore | Si/Al | P/Al |
| Fresh SAPO-34 | 0.148 | 0.101 | 0.090 | 2.47 | 0.41 |
| 720° C. regen | 0.052 | 0.050 | 0.038 | | |
| 620° C. regen | | 0.082 | 0.041 | 10.91 | 0.45 |
| 520° C. regen | 0.071 | 0.080 | 0.040 | | |

Temperature: 435° C. at inlet
Pressure: 34.5 kPa
WHSV: 2.5 $hr^{-1}$ (g $CH_3OH$/g SAPO-34)
Feed: 80 wt-% $CH_3OH$ + 20 wt-% $H_2O$
Catalyst Loading: 10 grams
Aluminum Phosphate: 5 grams A fourth example confirms the negative effect of silicon on an olefin cracking catalyst. A series of silicon deposition experiments was conducted in the following manner. Hexamethylcyclotrisiloxane (HMCTS) was spiked to a typical olefin cracking feed (i.e. FCC LCN, light cracked naphtha). The amount of HMCTS was calculated so that 0.1 wt % and 1.0 wt % Si, (as silicon), was deposited on the OCP catalyst during the 4 hours run, assuming 100% adsorption of HMCTS on the OCP catalyst. The HMCTS concentration in the feed was 28 & 280 ppm as silicon, for 0.1 and 1.0% silicon deposition, respectively. The spiked feed was passed over the OCP catalyst at the following conditions: temperature 570° C., 48.3 kPa pressure, 8.8 hr$^{-1}$ WHSV. Following silicon deposition, the samples were studied by infrared spectroscopy (IR). The absence of the characteristic Si—CH3 band shows that the HMCTS did decompose at 580° C., either partially, or totally. To complete the HMCTS decomposition to silica, a calcination step was performed, using an air/nitrogen mixture, at 585° C. Quantitative evaluation of how much silicon was on the catalyst surface after the deposition/calcinations was challenging because the OCP catalyst, from a chemical analysis point of view, is 99% silica, and therefore, adding a small amount of silica via deposition/calcinations would not change its chemical composition. The evaluation of the damaging effect of silicon deposition was done using the pilot plant test, at the following conditions: 40% isobutylene/60% isobutane feed, 585° C. inlet temperature, 48.3 kPa pressure, and 13.5 hr$^{-1}$ WHSV feed rate. The data presented in Table 3, include a comparative experiment using the fresh catalyst. Numbers are average per 20 hours run. It is clear that silicon has a damaging effect on the OCP catalyst, since both conversion and propylene/ethylene yields decline. The degree of yield decline correlates with the amount of silicon deposited, i.e., much greater catalyst deactivation was observed for 1% deposited silicon catalyst than for 0.1% deposited.

TABLE 3

|  | Fresh OCP catalyst | 0.1% Si deposited | 1.0% Si deposited |
| --- | --- | --- | --- |
| C$_4$-C$_6$ Olefins Conversion, wt-% | 49.0 | 46.4 | 33.5 |
| Propylene Yield, wt-% | 14.1 | 13.4 | 10.4 |
| Ethylene Yield, wt-% | 3.4 | 3.1 | 1.9 |

In the practice of the present invention, preferably at least about 60% of the active sites are retained despite exposure to contaminants, more preferably at least 75% of the active sites are retained, even more preferably at least 90% of the active sites are retained and most preferably at least 95% of the active sites on the catalyst are retained and not poisoned by contaminants after the catalyst has been in service for 2 years. Likewise, the numbers in Table 4 which corresponds to 95% retention of sites is the "most preferable case", 90% retention (i.e. numbers will be twice higher) is "more preferable" and 70 or 60% retention is "preferable". In the practice of the present invention, 95% of active sites on the catalyst must be retained (i.e. not poisoned) after 2 years of service. Three contaminants were considered in these examples—phosphorous, silica and sodium (for the former two, the nature of active species is not known exactly, therefore, they were counted them as phosphorous and silicon), and two different types of reactions—olefin cracking and methanol to olefin catalysts. The olefin cracking catalysts have significantly fewer active sites than the methanol to olefin catalysts. In catalytic naphtha cracking there are also a low number of active sites. It was calculated that a typical catalyst would be significantly affected by exposure to contaminants/poisons in amounts shown in Table 4.

TABLE 4

| Criteria (delta between fresh and Steamed Gamma-Alumina, in Unit of ppm) | | | | |
| --- | --- | --- | --- | --- |
|  | Good | Preferred | More Preferred | Most Preferred |
| Si | 20,000 | 10,000 | 5,000 | 1,000 |
| P | 1,000 | 500 | 50 | 10 |
| Na | 1,000 | 500 | 50 | 10 |
| Mg | 500 | 250 | 25 | 5 |
| Ca | 500 | 250 | 25 | 5 |

An alternate process for determining acceptable refractory materials to be used is as follows: The refractory sample is prepared by first crushing a refractory material and sieving out a 3.5-8 mesh portion. Then the sample is immersed in de-ionized water (100 g refractory/1 L DiH$_2$O) and it is treated it in an ultrasonic bath for 60 minutes. Then the sample is filtered to remove the water and dried at 120° C. overnight (15 hrs). The steaming procedure comprises first loading 5 grams of low silica containing gamma alumina (<150 ppm Si, <10 ppm P, <50 ppm Na, <10 ppm Ca, <10 ppm Mg) at the bottom of a steel reactor made of a nickel chromium ally such as Incoloy 600, manufactured by Special Metals Corporation, Huntington, W. Va., USA. Then 40 grams of the above pretreated refractory material is loaded on top of the gamma alumina. The refractory is then steamed at 650° C., 0 kPa (0 psig), 100 g/hr water addition, 250 cc/min (0.5 SCFH) N$_2$, for 100 hrs. The next step is the analysis process comprising after steaming, drying the sample by purge with N$_2$. Then the sample is cooled and the refractory material and gamma alumina are carefully separated with care taken to make sure there are no refractory particles in the gamma alumina. The gamma alumina is ground to a fine powder using boron carbide mortar and pestle to avoid Si and other element contamination. Then the ground gamma alumina sample is sent for ICP analysis (Si, P, Na, Ca, and Mg). The same analysis is done on a sample of the starting gamma alumina and the difference is calculated for before and after steaming.

This experiment involves the mixing of commercial refractory materials (Resco AA-22S from Resco Products, PA or Actchem 16344CA from Vesuvius, Ohio) with a SAPO-34 catalyst. Three samples of catalyst were used. In the first example, designated as Sample A, 25 grams of spray dried MTO catalyst was steamed at 650° C., 414 kPa (60 psig) and 100 g H$_2$O/hr for 100 hrs. Sample B comprised 25 grams of spray dried MTO catalyst mixed with 5 grams (40-60 mesh) of commercial refractory material (Actchem 16344CA from Vesuvius, Ohio) and then steamed at 650° C., 414 kPa (60 psig) and 100 g H$_2$O/hr for 100 hrs. Sample C was 25 grams of spray dried MTO catalyst that was mixed with 5 grams (40-60 mesh) of commercial refractory material (Resco AA-22S from Resco Products, PA, OH) and then steamed at 650° C., 414 kPa (60 psig) and 100 g H$_2$O/hr for 100 hrs.

After separating the catalyst from the refractory materials via sieving, samples A, B and C were performance tested in standard pilot plant test with the same conditions as for Table 2:

Performance of the three catalysts is listed below. HOS stands for the time it takes to reach 99% (CH$_3$OH+CH$_3$O CH$_3$) conversion. Selectivity of each component is reported at 99% (CH$_3$OH+CH$_3$O CH$_3$) conversion.

TABLE 5

| Selectivity at 99% Conversion (Mol-%) | | | |
| --- | --- | --- | --- |
| | Sample A | Sample B | Sample C |
| HOS | 2.4 | 2.6 | 2.5 |
| $C_2^=$ | 45.2 | 45.2 | 45.4 |
| $C_3^=$ | 37.4 | 37.4 | 37.3 |
| $C_2^=+C_3^=$ | 82.6 | 82.6 | 82.8 |
| $C_4s$ | 10.3 | 10.5 | 10.2 |
| $C_5^+$ | 3.9 | 3.9 | 3.9 |
| $C_1$ | 2.4 | 2.3 | 2.4 |
| $C_2$ | 0.4 | 0.4 | 0.4 |
| $C_3$ | 0.3 | 0.3 | 0.3 |
| $C_2^=/C_3^=$ | 1.21 | 1.21 | 1.22 |

From the data above, it is clear that mixing of the commercial refractory materials with MTO catalyst does not cause harm to MTO catalyst. These refractory materials have low rate of Si, P, Na, Ca or Mg leach rate.

Having now fully described this invention, it will be appreciated by those skilled in the art that the invention can be performed within a wide range of parameters within what is claimed, without departing from the spirit and scope of the invention.

What is claimed is:

1. A reaction zone for use of an acidic catalyst under reaction conditions including operation of said reaction zone at temperatures from 350° to 650° C. wherein said reaction zone comprises at least one reactor and wherein said reactor surfaces comprise materials selected from the group consisting of silicon, phosphorus, alkali metals and alkali earth metals wherein after said operation of said reaction zone, said reactor surfaces retain sufficient quantities of said materials so as to maintain catalyst performance.

2. The reaction zone of claim 1 wherein said material leaches less than 20,000 ppm silicon, less than 1,000 ppm phosphorus, less than 1,000 ppm sodium, less than 500 ppm magnesium and less than 500 ppm calcium when said material is subjected to steaming at 650° C., 0 kPa, 100 g/hr water addition, 250 cc/min nitrogen for 100 hours.

3. The reaction zone of claim 1 wherein said material leaches less than 10,000 ppm silicon, less than 500 ppm phosphorus, less than 500 ppm sodium, less than 250 ppm magnesium and less than 250 ppm calcium when said material is subjected to steaming at 650° C., 0 kPa, 100 g/hr water addition, 250 cc/min nitrogen for 100 hours.

4. The reaction zone of claim 1 wherein said material leaches less than 5,000 ppm silicon, less than 50 ppm phosphorus, less than 50 ppm sodium, less than 25 ppm magnesium and less than 25 ppm calcium when said material is subjected to steaming at 650° C., 0 kPa, 100 g/hr water addition, 250 cc/min nitrogen for 100 hours.

5. The reaction zone of claim 1 wherein said material leaches less than 1,000 ppm silicon, less than 10 ppm phosphorus, less than 10 ppm sodium, less than 5 ppm magnesium and less than 5 ppm calcium when said material is subjected to steaming at 650° C., 0 kPa, 100 g/hr water addition, 250 cc/min nitrogen for 100 hours.

* * * * *